US008008835B2

(12) United States Patent
Degertekin

(10) Patent No.: US 8,008,835 B2
(45) Date of Patent: Aug. 30, 2011

(54) MULTIPLE ELEMENT ELECTRODE CMUT DEVICES AND FABRICATION METHODS

(75) Inventor: F. Levent Degertekin, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 671 days.

(21) Appl. No.: 11/068,005

(22) Filed: Feb. 28, 2005

(65) Prior Publication Data
US 2005/0200241 A1 Sep. 15, 2005

Related U.S. Application Data

(60) Provisional application No. 60/548,193, filed on Feb. 27, 2004, provisional application No. 60/611,049, filed on Sep. 16, 2004.

(51) Int. Cl.
H02N 1/08 (2006.01)
(52) U.S. Cl. ........................................................ 310/309
(58) Field of Classification Search .................. 310/309, 310/322, 324, 330, 332, 334, 365, 366; 600/459; 381/174; 361/174
See application file for complete search history.

(56) References Cited

U.S. PATENT DOCUMENTS

| | | | |
|---|---|---|---|
| 4,794,384 A | 12/1988 | Jackson | |
| 5,129,262 A | 7/1992 | White et al. | |
| 5,158,087 A | 10/1992 | Gatzke | |
| 5,560,362 A | 10/1996 | Sliwa, Jr. et al. | |
| 5,585,546 A | 12/1996 | Gururaja et al. | |
| 5,606,974 A | 3/1997 | Castellano et al. | |
| 5,677,823 A * | 10/1997 | Smith | 361/234 |
| 5,679,888 A | 10/1997 | Tohda et al. | |
| 6,122,338 A | 9/2000 | Yamauchi | |
| 6,122,538 A | 9/2000 | Sliwa, Jr. et al. | |
| 6,178,033 B1 | 1/2001 | Ford et al. | |
| 6,201,900 B1 | 3/2001 | Hossack et al. | |
| 6,246,482 B1 | 6/2001 | Kinrot et al. | |
| 6,254,831 B1 | 7/2001 | Barnard et al. | |
| 6,262,946 B1 | 7/2001 | Khuri-Yakub et al. | |
| 6,292,435 B1 | 9/2001 | Savord et al. | |

(Continued)

FOREIGN PATENT DOCUMENTS

JP 52-049688 A1 4/1977

(Continued)

OTHER PUBLICATIONS

J. Knight, J. McLean, and F.L. Degertekin, *Low Temperature Fabrication of Immersion Capacitive Micromachined Ultrasonic Transducers on Silicon and Dielectric Substrates,* IEEE Transactions on UFFC, vol. 51, No. 10, pp. 1324-1333, Oct. 2004.

(Continued)

*Primary Examiner* — Derek J Rosenau
(74) *Attorney, Agent, or Firm* — Troutman Sanders LLP; Robert R. Elliott, Jr.

(57) ABSTRACT

Multiple electrode element capacitive micromachined ultrasonic transducer ("cMUT") devices and fabrication methods are provided. A cMUT device generally comprises a top electrode disposed within a membrane, a bottom electrode disposed on a substrate, and a cavity between the membrane and the bottom electrode. In a preferred embodiment of the present invention, at least one of the first electrode and the second electrode comprises a plurality of electrode elements. The electrode elements can be positioned and energized to shape the membrane and efficiently transmit and receive ultrasonic energy, such as ultrasonic waves. Other embodiments are also claimed and described.

28 Claims, 7 Drawing Sheets

U.S. PATENT DOCUMENTS

| | | | |
|---|---|---|---|
| 6,314,057 | B1 | 11/2001 | Solomon et al. |
| 6,320,239 | B1 | 11/2001 | Eccardt et al. |
| 6,328,696 | B1 | 12/2001 | Fraser |
| 6,330,057 | B1 | 12/2001 | Lederer et al. |
| 6,338,716 | B1 | 1/2002 | Hossack et al. |
| 6,426,582 | B1 | 7/2002 | Niederer et al. |
| 6,441,449 | B1 * | 8/2002 | Xu et al. .................. 257/414 |
| 6,445,109 | B2 | 9/2002 | Percin et al. |
| 6,461,299 | B1 | 10/2002 | Hossack |
| 6,483,056 | B2 * | 11/2002 | Hyman et al. ............. 200/181 |
| 6,504,795 | B1 | 1/2003 | Niederer et al. |
| 6,511,427 | B1 | 1/2003 | Sliwa, Jr. et al. |
| 6,514,214 | B2 | 2/2003 | Kokate et al. |
| 6,558,330 | B1 | 5/2003 | Ayter et al. |
| 6,562,650 | B2 | 5/2003 | Ladabaum |
| 6,571,445 | B2 | 6/2003 | Ladabaum |
| 6,604,425 | B1 | 8/2003 | Hsu et al. |
| 6,632,178 | B1 | 10/2003 | Fraser |
| 6,639,339 | B1 | 10/2003 | Bernstein |
| 6,659,954 | B2 | 12/2003 | Robinson |
| 6,669,644 | B2 | 12/2003 | Miller |
| 6,684,469 | B2 | 2/2004 | Horning et al. |
| 6,707,351 | B2 | 3/2004 | Gorrell |
| 6,714,484 | B2 | 3/2004 | Ladabaum et al. |
| 6,787,970 | B2 | 9/2004 | Shim et al. |
| 6,789,426 | B2 | 9/2004 | Yaralioglu et al. |
| 6,831,394 | B2 | 12/2004 | Baumgartner et al. |
| 6,853,041 | B2 | 2/2005 | Khuri-Yakub et al. |
| 7,030,536 | B2 | 4/2006 | Smith et al. |
| 7,166,486 | B2 | 1/2007 | Ohtaka et al. |
| 7,612,483 | B2 | 11/2009 | Degertekin |
| 7,646,133 | B2 | 1/2010 | Degertekin |
| 7,670,290 | B2 | 3/2010 | Hossack et al. |
| 7,762,954 | B2 | 7/2010 | Nix et al. |
| 2002/0009015 | A1 | 1/2002 | Laugharn et al. |
| 2002/0039463 | A1 | 4/2002 | Degertekin et al. |
| 2002/0048219 | A1 | 4/2002 | Ladabaum et al. |
| 2002/0074553 | A1 | 6/2002 | Starikov et al. |
| 2002/0074621 | A1 * | 6/2002 | Cheng et al. .................. 257/532 |
| 2002/0123749 | A1 | 9/2002 | Jain |
| 2002/0135329 | A1 * | 9/2002 | Neufeld et al. ............. 318/116 |
| 2003/0029242 | A1 | 2/2003 | Yaralioglu et al. |
| 2003/0114760 | A1 | 6/2003 | Robinson |
| 2004/0002655 | A1 | 1/2004 | Bolorforosh et al. |
| 2004/0075364 | A1 | 4/2004 | Mehta |
| 2004/0085858 | A1 | 5/2004 | Khuri-Yakub et al. |
| 2004/0113524 | A1 | 6/2004 | Baumgartner et al. |
| 2004/0174773 | A1 | 9/2004 | Thomenius et al. |
| 2004/0180466 | A1 | 9/2004 | Foglietti et al. |
| 2004/0236223 | A1 | 11/2004 | Barnes et al. |
| 2004/0267134 | A1 | 12/2004 | Hossack et al. |
| 2005/0046311 | A1 | 3/2005 | Baumgartner et al. |
| 2005/0096546 | A1 | 5/2005 | Hazard et al. |
| 2005/0121734 | A1 | 6/2005 | Degertekin et al. |
| 2005/0177045 | A1 | 8/2005 | Degertekin et al. |
| 2005/0200241 | A1 | 9/2005 | Degertekin |
| 2005/0200242 | A1 | 9/2005 | Degertekin |
| 2005/0203397 | A1 | 9/2005 | Degertekin |
| 2006/0075818 | A1 | 4/2006 | Huang et al. |
| 2006/0116585 | A1 | 6/2006 | Nguyen-Dinh et al. |
| 2009/0182229 | A1 | 7/2009 | Wodnicki |
| 2010/0249605 | A1 | 9/2010 | Degertekin |
| 2010/0256501 | A1 | 10/2010 | Degertekin |
| 2010/0268089 | A1 | 10/2010 | Degertekin |

FOREIGN PATENT DOCUMENTS

| | | |
|---|---|---|
| WO | 01/44765 | 6/2001 |
| WO | 2003011749 A2 | 2/2002 |
| WO | 2004/016036 | 2/2004 |
| WO | 2005084267 A2 | 9/2005 |

OTHER PUBLICATIONS

J. McLean and F.L. Degertekin, *Interdigital Capacitive Micromachined Ultrasonic Transducers for Sensing and Pumping in Microfluidic Applications,* Proceedings of the 12th International Conference on Solid State Sensors and Actuators, pp. 915-918, Jun. 2003.

J. Knight and F.L. Degertekin, *Fabrication and Characterization of cMUTs for Forward Looking Intravascular Imaging,* Proceedings of 2003 IEEE Ultrasonics Symposium, pp. 577-580, Oct. 2003.

N. A. Hall, R. Guldiken, J. McLean, and F.L. Degertekin, *Modeling and Design of cMUTs using Higher Order Vibration Modes,* Proceedings of 2004 IEEE Ultrasonics Symposium, pp. 260-263, 2004.

J. McLean, R. Guldiken, and F.L. Degertekin, *CMUTs with Dual Electrode Structure for Improved Transmit and Receive Performance,* Proceedings of 2004 IEEE Ultrasonics Symposium, pp. 501-504, Aug. 2004.

U. Demirci, A.S. Ergun, O. Oralkan, M. Karaman, B.T. Khuri-Yakub, *Forward-Viewing CMUT Arrays for Medical Imaging,* IEEE Transactions on UFFC, vol. 51, No. 7, pp. 886-894, Jul. 2004.

J. Knight and F. L. Degertekin, *Capacitive Micromachined Ultrasonic Transducers for Forward Looking intravascular Imaging Arrays,* Proceedings of 2002 IEEE Ultrasonics Symposium, pp. 1079-1082, 2002.

X.C. Jin, I. Ladabaum, F.L. Degertekin, S. Calmes and B.T. Khuri-Yakub, *Fabrication and Characterization of Surface Micromachined Capacitive Ultrasonic Immersion Transducers,* IEEE Journal of Microelectromechanical Systems, vol. 8, No. 1, pp. 100-114, Mar. 1999.

S. Calems, C. Cheng, F.L. Degertekin, X.C. Jin, S. Ergun and B.T. Khuri-Yakub, *Highly Integrated 2-D Capacitive Micromachined Ultrasonic Transducers,* Proceedings of 1999 IEEE Ultrasonics Symposium, pp. 1163-1166, 1999.

W. Lee, N. A. Hall, Z. Zhou, and F. L. Degertekin, *Fabrication and Characterization of a Micromachined Acoustic Sensor with Integrated Optical Readout,* IEEE Journal of Selected Topics on Quantum Electronics, vol. 10, No. 3, pp. 643-651, May/Jun. 2004.

European Patent Office Communication Relating to the Results of the Partial International Search Relating to International Patent Application No. PCT/US2005/008259, Aug. 25, 2005.

Jeff McLean and F. Levent Degertekin, *Capacitive Micromachined Ultrasonic Transducers With Asymmetric Membranes for Microfluidic Applications,* 2001 IEEE Ultrasonics Symposium, pp. 925-928 (0-7803-7177-1/01).

Notification of the Transmittal of International of the International Search Report and the Written Opinion of the International Search Authority, European Patent Office, Oct. 31, 2005.

International Search Report for PCT/US2005/06408 dated Sep. 5, 2007.

PCT International Search Report and Written Opinion Concerning Application No. PCT/US05/03898 dated Dec. 27, 2006.

PCT International Search Report and Written Opinion Concerning Application No. PCT/US05/06408 dated Dec. 27, 2007.

PCT International Search Report and Written Opinion Concerning Application No. PCT/US04/037089 dated Feb. 7, 2008.

PCT International Search Report and Written Opinion Concerning Application No. PCT/US05/06474 dated Oct. 16, 2006.

Supplementary European Search Report for European Application No. EP05724089 dated Jul. 9, 2010.

Office Action dated Oct. 18, 2010 issued by the Japanese Patent Office for related Japanese Patent Application No. 2007-503069.

* cited by examiner

MULTIPLE ELEMENT ELECTRODE CMUT DEVICES AND FABRICATION METHODS

CROSS REFERENCE TO RELATED APPLICATIONS AND PRIORITY CLAIMS

This application claims the benefit of U.S. Provisional Application No. 60/548,193, filed 27 Feb. 2004, and U.S. Provisional Application No. 60/611,049, filed 16 Sep. 2004.

TECHNICAL FIELD

The present invention relates generally to chip fabrication, and more particularly, to fabricating capacitive micromachined ultrasonic transducers ("cMUTs") having multiple-element electrodes and cMUT imaging arrays incorporating cMUTs having multiple-element electrodes.

BACKGROUND

Capacitive micromachined ultrasonic transducer ("cMUT") devices generally combine mechanical and electronic components in very small packages. The mechanical and electronic components operate together to transform mechanical energy into electrical energy and vice versa. Because cMUTs are typically very small and have both mechanical and electrical parts, they are commonly referred to as micro-electronic mechanical systems ("MEMS") devices.

Conventional cMUTs generally have a ground electrode and a hot electrode. The hot electrode can be used to transmit and receive ultrasonic acoustical waves during ultrasonic imaging. Due to the differing characteristics associated with transmitting and receiving ultrasonic waves, conventional cMUT hot electrodes are commonly optimized to receive or transmit ultrasonic waves with high sensitivity while the maximum transmit power is compromised. This optimization results in sacrificed device performance for the non-optimized action, ultimately sacrificing the quality of data sent or collected by a cMUT having a hot electrode only optimized for receiving or transmit waves.

One approach to address this problem includes using two cMUTs placed side by side. One of the cMUTs can be optimized for transmitting ultrasonic waves while the other cMUT can be optimized for receiving ultrasonic waves. This approach, while addressing the problems associated with a hot electrode optimized for transmitting or receiving ultrasonic waves, has several drawbacks. For example, a major drawback associated with this solution includes the amount of space sacrificed when two cMUTs are used to transmit and receive ultrasonic waves instead of one. cMUTs are often desirable for small scale applications and the increased space associated with using multiple cMUTs would greatly diminish the desirability of using cMUTs.

Another problem associated with conventional cMUTs is that they have lower maximum transmit pressures relative to piezoelectric ultrasonic transducers. Higher transmit pressures are generally desirable to increase signal penetration and to increase the force of ultrasonic waves reflected from media being imaged. In conventional cMUT operation, where the membrane is moved from a rest position to near collapse, the output pressure is limited because the displacement is limited to the one third of the initial gap. To increase the output transmission pressure output for cMUTs to, for example, 1 MPa (Mega-Pascal), which is desired for medical imaging applications, collapse and collapse-snap back operation states for cMUT membranes have been proposed. These proposed approaches, while increasing cMUT output transmit pressures, are nonlinear operational modes limiting the transmit signal shapes, and can cause severe dielectric charging because of the frequent contact between dielectric layers during operation.

Another problem associated with conventional cMUTs is the difficulty in controlling the shape of a cMUT membrane. Since the geometrical shape of a cMUT membrane largely affects overall cMUT device performance, it is desirable to control a cMUT membrane's shape when transmitting and receiving ultrasonic waves.

An additional disadvantage to conventional cMUTs includes the complicated switching circuitry and signal generation and detection circuitry that must be used in concert with the single receive and transmit cMUT electrode. Typically, complicated circuitry is required for single receive and transmit cMUT electrode because protection circuits must be utilized to prevent large transmit signals to be input to the receiver amplifier. These protection circuits increase the parasitic capacitance in parallel with the cMUT, further degrading the received signal. The switching transients may saturate the receiving amplifier and result in dead zones in the images where the regions close to the transducer array can not be imaged.

Therefore, there is a need in the art for a cMUT fabrication method enabling fabrication of a cMUT with at least one multiple-element electrode to increase and enhance cMUT device performance.

Additionally, there is a need in the art for fabricating cMUTs having controllable membranes to increase and enhance cMUT device performance.

Additionally, there is a need in the art for a cMUT device having multiple hot electrodes or separate transmit and receive electrodes so transmitting and receiving ultrasonic wave functions can be simultaneously optimized.

Still yet, there is a need for cMUTs capable of generating multiple output signals from a single transmit event and utilizing the different frequency content of output signals.

It is to the provision of such cMUT fabrication and cMUT imaging array fabrication that the embodiments of present invention are primarily directed.

BRIEF SUMMARY OF THE INVENTION

The present invention comprises multiple-element cMUT array transducer fabrication methods and systems. The present invention provides cMUTs for imaging applications that have multiple-element electrodes for optimizing the transmission and receipt of ultrasonic waves, which can be especially useful in medical imaging applications. The cMUTs of the present invention can also be adapted to generate multiple receive signals from single transmit event by utilizing the frequency content of received signals. The cMUTs can be fabricated on dielectric or transparent substrates, such as, but not limited to, silicon, quartz, or sapphire, to reduce device parasitic capacitance, thus improving electrical performance and enabling optical detection methods to be used, although other translucent of opaque materials can be used. Additionally, cMUTs constructed according to the present invention can be used in immersion applications such as intravascular catheters and ultrasound imaging.

The cMUTs fabricated in accordance with the present invention can comprise a cMUT proximate a substrate. The substrate can be a silicon substrate or formed from transparent materials. A circuit can be embedded in the substrate or located proximate the substrate to receive and direct optical or electric signals to and from the cMUT. The cMUTs can also comprise at least one multiple-element electrode, which can aid in shaping the cMUT and in providing an optimal membrane shape for transmitting and receiving ultrasonic waves. The multiple-element electrode can also receive and transmit ultrasonic waves. By properly controlling or adjusting a cMUT membrane's shape when transmitting and receiving ultrasonic waves, it is possible to increase image resolution, enhance transmission signal depth penetration, increase transmit output pressure, and generate multiple output signals with different frequency content.

In a preferred embodiment, the present invention is a cMUT comprising a multi-element first electrode having a first electrode element and a second electrode element, wherein the first and second electrode elements are adapted to transmit an ultrasonic wave. The first electrode element and the second electrode element are typically physically separated, but can be electrically coupled. The multi-element first electrode can be disposed within a membrane. The multi-element first electrode can be disposed proximate a substrate.

The preferred cMUT has a flexible membrane and a membrane shaping means, the membrane shaping means preferably being at least one of the first electrode element and the second electrode element. The cMUT can further include a bottom electrode, wherein the membrane and the bottom electrode are separated by a gap distance in an electrically neutral state, and wherein a side electrode element pair is adapted to flex the membrane by more than one third of the gap distance during transmission of an ultrasonic wave.

A method of transceiving ultrasonic waves according to another embodiment of the present invention preferably comprises the steps of providing a cMUT having a multi-element first electrode incorporating a first electrode element and a second electrode element, the first electrode element separate from the second electrode element, and applying a first voltage to the first electrode element and the second electrode element to transmit an ultrasonic wave. The preferred method of transceiving ultrasonic waves can further include the step of applying a bias voltage to the first electrode element and the second electrode element to receive an ultrasonic wave signal, the step of optically sensing the received ultrasonic wave signal, and the step of electrically sensing the received ultrasonic wave signal.

A method of fabricating a cMUT according to another embodiment of the present invention comprises the steps of providing a top conductor, providing a bottom conductor separated by a gap distance from the top conductor, and configuring at least one of the top and bottom conductors into a plurality of electrode elements physically separated from one another, although at later fabrication steps, two or more of the electrode elements can be electrically coupled. The top and bottom conductor can be formed of the same material(s), or different material(s). The top and bottom conductors can be adapted to both transmit and receive ultrasonic signals.

The method of fabricating the cMUT can further comprise the steps of providing a sacrificial layer proximate the first conductor, providing a first membrane layer proximate the sacrificial layer, providing a second membrane layer proximate the second conductor, and removing the sacrificial layer.

Another preferred embodiment of the present invention includes a cMUT comprising a first electrode that incorporates a first electrode element and a second electrode element proximate the first electrode element. An electrode having a plurality of elements in accordance with the present invention can efficiently transmit and receive ultrasonic wave signals. The electrode elements can be used both to transmit and aid in shaping a cMUT membrane so that the cMUT is optimized for transmitting and receiving ultrasonic acoustical waves. A preferred embodiment of the present invention can utilize leveraged bending to increase the membrane displacement from one third of the initial cMUT cavity to nearly the entire initial cMUT without collapse.

In another preferred embodiment of the present invention, a method to fabricate a cMUT comprises providing a first conductive layer, providing a second conductive layer, and patterning one of the first and second conductive layers into a plurality of electrode elements. The first conductive layer can be proximate the substrate, and can be isolated from the second conductive layer. A cMUT fabrication method can also comprise providing a sacrificial layer proximate the first conductive layer, providing a first membrane layer proximate the sacrificial layer, providing a second membrane layer proximate the second conductive layer, and removing the sacrificial layer to form a cavity. The multiple elements of the first conductive layer and the second conductive layer can be isolated from each other by enveloping the multiple elements in a dielectric material, such as silicon nitride. While the multiple elements are physically separate one from another, later fabrication may electrically couple two or more elements.

In yet another preferred embodiment of the present invention, a method of transceiving an ultrasonic wave using a cMUT comprises applying a first bias voltage to a first electrode element to increase a gap distance and applying an AC signal to a first electrode element to transmit an ultrasonic wave. The method can further comprise applying a second bias voltage to the first electrode element to decrease the gap distance and receiving an ultrasonic wave signal.

This configuration has several advantages including, but not limited to, the maximum pressure amplitude during transmit mode can be significantly increased. By locating the transmit electrodes near the edges of the membrane, leveraged bending can increase the maximum displacement without collapsing the membrane.

In yet another preferred embodiment, the present invention is a cMUT comprising a multi-element first electrode having a first electrode element and a second electrode element, wherein the first and second electrode elements are adapted to shape a membrane.

These and other features as well as advantages, which characterize the various preferred embodiments of present invention, will be apparent from a reading of the following detailed description and a review of the associated drawings.

Figure 1:
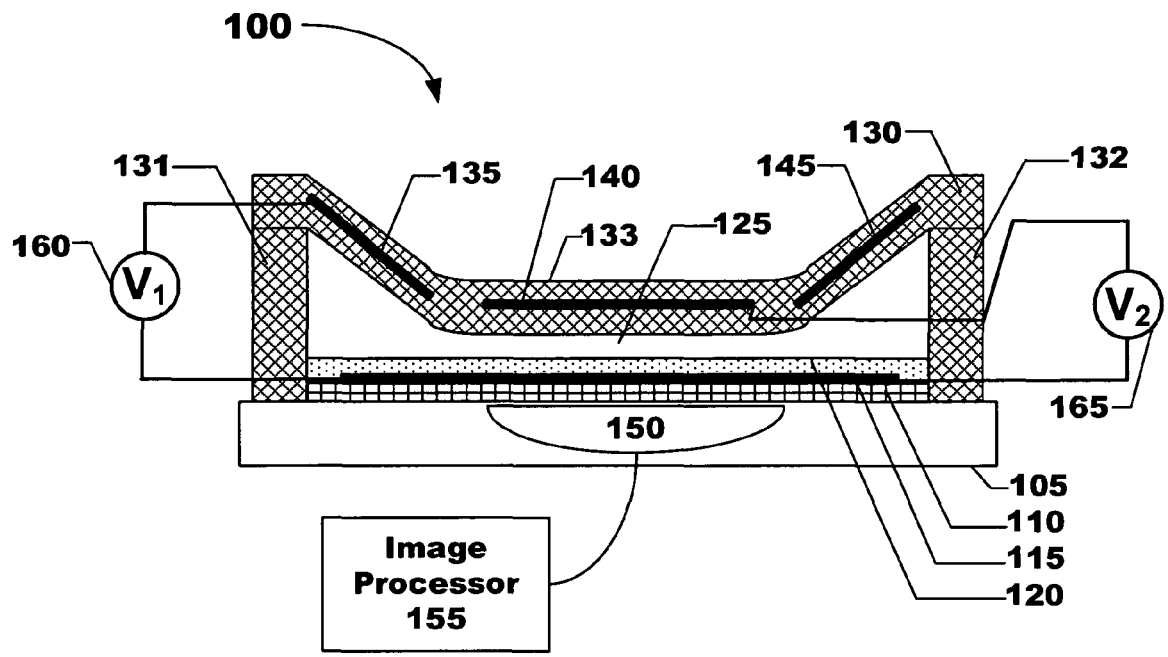
FIG. 1 illustrates a cross-sectional view of a cMUT having a multi-element top electrode in accordance with a preferred embodiment of the present invention.

DETAILED DESCRIPTION OF PREFERRED EMBODIMENTS cMUTs have been developed as an alternative to piezoelectric ultrasonic transducers particularly for micro-scale and array applications. cMUTs are typically surface micromachined and can be fabricated into one or two-dimensional arrays and customized for specific applications. cMUTs can have performance comparable to piezoelectric transducers in terms of bandwidth and dynamic range.

A cMUT typically incorporates a top electrode disposed within a membrane suspended above a conductive substrate or a bottom electrode proximate or coupled to a substrate. An adhesion layer or other layer can optionally be disposed between the substrate and the bottom electrode. The membrane can have elastic properties enabling it to fluctuate in response to stimuli. For example, stimuli can include external forces exerting pressure on the membrane and electrostatic forces applied through cMUT electrodes.

cMUTs can transmit and receive acoustical waves. To transmit an acoustic wave, an AC signal and a large DC bias voltage can be applied to a cMUT electrode disposed within a cMUT membrane. Alternatively, the voltages can be applied to a bottom electrode. The DC voltage can pull down the membrane where the transduction is efficient and can linearize a cMUT's response. The AC voltage can set a membrane into motion at a desired frequency to generate an acoustic wave in a surrounding medium, such as gases or fluids. To receive an acoustic wave, a capacitance change can be measured between cMUT electrodes when an impinging acoustic wave sets a cMUT membrane into motion.

The present invention provides cMUTs comprising at least one multiple-element electrode. The top electrode and the bottom electrode can both be fabricated to have multiple-elements. Preferably, only one of the top electrode or the bottom electrode has multiple elements. In some embodiments, both the top electrode and the bottom electrode can have multiple elements. The multiple-element electrode can aid in controlling a cMUT to maximize both transmission and receipt of acoustical waves. cMUTs having multiple-element electrodes can aid in shaping or altering cMUT membranes for optimal signal transmission and receipt when varying signals are applied to multi-element electrodes.

Exemplary equipment for fabricating cMUTs according to the present invention can include a PECVD system, a dry etching system, a metal sputtering system, a wet bench, and photolithography equipment. cMUTs fabricated according to the present invention generally include materials deposited and patterned on a substrate in a build-up process. The present invention can utilize low-temperature PECVD processes for depositing various silicon nitride layers at approximately 250 degrees Celsius, which is preferably the maximum process temperature when a metal sacrificial layer is used. Alternatively, the present invention according to other preferred embodiments can utilize an amorphous silicon sacrificial layer deposited as a sacrificial layer at approximately 300 degrees Celsius.

Referring now the drawings, in which like numerals represent like elements, preferred embodiments of the present invention are herein described.

FIG. 1 illustrates a cross-sectional view of a cMUT 100 having a multi-element top electrode in accordance with a preferred embodiment of the present invention. The cMUT 100 comprises various material layers proximate a substrate 105. The substrate 105 can comprise silicon and can also comprise materials enabling optical detection methods, preferably transparent materials, to be utilized in accordance with the present invention. The material layers can include an adhesion layer 110, a bottom electrode 115, an isolation layer 120, a membrane 130, and a top electrode layer configured into multiple electrode elements 135, 140, 145. The bottom electrode 115 and top electrode elements 135, 140, 145 can be many conductive materials, such as conductive metals or a doped surface of silicon substrate. As discussed in greater detail below, the top electrode layer forming the multiple electrode elements 135, 140, 145 is generally deposited then configured into the multiple electrode elements 135, 140, 145.

Figure 2:
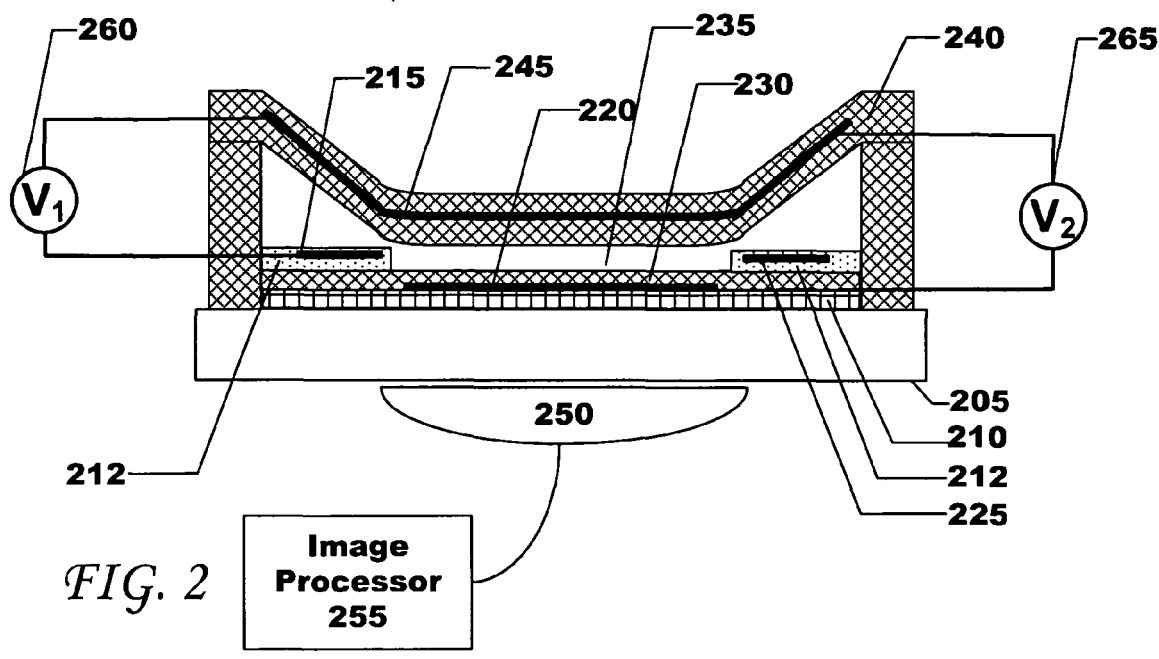
FIG. 2 illustrates a cross-sectional view of a cMUT having a multi-element bottom electrode in accordance with a preferred embodiment of the present invention.

The substrate 105 can be formed of silicon and can contain signal generation and reception circuits. For example, the substrate 105 can comprise an integrated circuit 150 embedded in the substrate 105 to enable the cMUT 100 to transmit and receive ultrasonic waves. FIG. 1 illustrates the integrated circuit 150 as embedded, while FIG. 2 illustrates an alternative embodiment wherein the circuit 250 is proximate the substrate, although not necessarily embedded in the substrate. The integrated circuit 150 can be adapted to generate and receive signals and provide the signals to an image processor 155. The integrated circuit 150 can contain both signal generation and reception circuitry or separate integrated generation and reception circuits can be utilized. The image processor 155 can process the signals and create an image from the signals.

The adhesion layer 110 can be placed on the substrate 105 and disposed between the substrate 105 and the bottom electrode 115. The adhesion layer 110 can be Chromium, or many other suitable materials, and is optional in some embodiments. For example, when a doped surface of a substrate, for example a silicon substrate, forms the bottom electrode 115 the adhesion layer 110 may not be utilized. The bottom electrode 115 is preferably fabricated from a conductive material such as Gold or Aluminum. The adhesion layer 110 can be used to adequately bond the bottom electrode 115 to the substrate 105.

The cMUT 100 can also comprise an isolation layer 120 and a cavity 125 defined by a membrane layer 130. The isolation layer 120 can be deposited on the bottom electrode 115, and can comprise silicon nitride. The isolation layer 120 can isolate the bottom electrode 115 from etchants used to form the cavity 125. The isolation layer 120 may not be utilized in some embodiments. As shown, the cavity 125 is generally disposed between the isolation layer 120 and the membrane 130. In embodiments without an isolation layer 120, the cavity 125 would generally be disposed between the bottom electrode 115 and the membrane 130. The cavity 125 can be formed by removing or etching a sacrificial layer generally disposed between the bottom electrode 115 and the membrane 130.

The membrane 130 can have elastic characteristics allowing it to move relative to the substrate 105. The membrane 130 can comprise silicon nitride and can be formed from multiple membrane layers. For example, the membrane 130 can be formed from a first membrane layer and a second membrane layer. In addition, the membrane layer 130 can have sides 131, 132 formed during fabrication by depositing various membrane layers and removing a sacrificial layer to form a cavity 125. As shown, the membrane 130 has a center area 133 generally located equally between the sides 131, 132.

In a preferred embodiment, the cMUT 100 can also comprise the top electrode layer being formed of multiple electrode elements 135, 140, 145 disposed within the membrane 130. Two or more of the multiple electrode elements 135, 140, 145 can be coupled to form an electrode element pair. Preferably, side electrode elements 135, 145 are formed nearer the sides 131, 132 of the membrane 130, and center electrode element 140 is formed nearer the center area 133 of the membrane 130. The electrode elements 135, 140, 145 can be fabricated using a conductive material, such as Gold or Aluminum. The side electrode elements 135 and 145 can be electrically coupled and isolated from the center electrode element 145 to form an electrode element pair in the electrode. The electrode elements 135, 140, 145 can be formed from the same conductive material and patterned to have predetermined locations and varying geometrical configurations within the membrane 130. The side electrode element pair 135, 145 can have a width less than the center electrode 140, and a portion of the pair 135, 145 can be placed at approximately the same distance from the substrate 105 as the center electrode element 140. In other embodiments, additional multiple electrode elements can be formed within the membrane 130 at varying distances from the substrate 105. In a preferred embodiment, each side electrode element 135, 145 has a volume approximately half of the volume of the center electrode element 140 so that the combined volume of the side electrode element pair 135, 145 is approximately equal to the volume of the center electrode element 140.

The electrode elements 135, 140, 145 can be adapted to transmit and receive ultrasonic energy, such as ultrasonic acoustical waves, by receiving signals from different voltage sources. The side electrode elements 135, 145 are shown provided with a first signal from a first voltage source 160 ($V_1$) and the center electrode 140 is shown provided with a second signal from a second voltage source 165 ($V_2$). The side electrode elements 135, 145 can be electrically coupled so that voltage or signal supplied to one of the electrode elements 135, 145 will be provided to the other of the electrode elements 135, 145. These signals can be voltages, such as DC bias voltages and AC signals. Preferably, the side electrode elements 135, 145 are adapted to shape the membrane 130 to have a large displacement swing forming a relatively large gap for the transmission of ultrasonic waves by the side electrode elements 135, 145. It is desirable to use a gap size that during transmission allows for greater transmission pressure. Further the side electrode elements 135, 145 can be adapted to shape the membrane 130 to form a relatively small gap for reception of ultrasonic waves by the center electrode element 140. It is desirable to use a gap size for reception that allows for greater sensitivity of the cMUT 100. Both the center electrode element 140 and the side electrode element elements 135, 145 can also receive and transmit ultrasonic energy, such as ultrasonic waves.

The cMUT 100 can be optimized for transmitting and receiving ultrasonic energy by altering the shape of the membrane 130. As discussed below in greater detail with reference to FIGS. 4A and 4B, the electrode elements 135, 140, 145 can be provided with varying bias voltages and signals to alter the shape of the membrane 130. Additionally, by providing the various voltages, the cMUT 100 can operate in two states: a transmission state and a reception state. For example, during a receiving state, the side electrode elements 135, 145 can be provided a bias voltage from the first voltage source 160 ($V_1$) to optimize the shape of the membrane 130 for receiving an acoustic ultrasonic wave using the center electrode element 140 while providing a bias voltage from a second voltage source 165 ($V_2$). The side electrode elements 135, 145 can also be used for receiving ultrasonic waves. Similarly, during a transmission state, the side electrode elements 135, 145 can be provided with an AC signal from the first voltage source 160 ($V_1$) in addition to a bias from the first voltage source 160 ($V_1$) to optimize the shape of the membrane 130 for transmitting an acoustic ultrasonic wave. An AC signal and a bias voltage may be applied by the second voltage source 165 ($V_2$) to the center electrode element 140 during the transmit state.

The first and second voltage sources 160, 165 ($V_1$, $V_2$) can be adapted to provide both AC and DC voltages to the electrode elements 135, 140, 145. These voltage sources 160, 165 ($V_1$, $V_2$) can be controlled by high voltage signal shaping circuitry commonly used in digital ultrasound imaging systems. Vias can be formed in the material layers of the cMUT 100 so that the signals from the first and second voltage sources 160, 165 ($V_1$, $V_2$) can be provided to the electrode elements 135, 140, 145.

FIG. 2 illustrates a cross-sectional view of a cMUT 200 having a multi-element bottom electrode in accordance with a preferred embodiment of the present invention. The cMUT 200 comprises various layers proximate a substrate 205. These layers can include an adhesion layer 210, a dielectric layer 212, a first side electrode element 215, a center electrode element 220, a second side electrode element 225, an isolation layer 230, a membrane 240, and a top electrode 245. The side electrode elements 215, 225 can be electrically coupled in some embodiments forming an electrode element pair of an electrode.

The substrate 205 can comprise silicon and can also comprise materials enabling optical detection methods to be utilized in accordance with the present invention. For example, transparent or translucent materials could be used to enable optical detection methods. The substrate 205 can be formed of silicon and an integrated circuit 250 can be proximate the substrate 205. The substrate 205 can be designed to enable the use of optical signals to transmit and detect capacitance changes associated with cMUT 200. For example, integrated circuit 250 can be adapted to generate and receive optical signals and provide the optical signals to an image processor 255. The image processor 255 can process the optical signals and create an image from the optical signals. Silicon and many other materials can have beneficial properties with respect to signals having predetermined optical wavelengths.

As illustrated in FIG. 2, the adhesion layer 210 can be placed on the substrate 205, and proximate the center electrode element 220. The adhesion layer 210 can be Chromium or many other materials adapted to adequately bond the bottom electrode elements 215, 220, 225 to the substrate 205. In some embodiments, an adhesion layer 210 may not be used if the bottom electrode elements 215, 220, 225 can adequately bond to the substrate 205 during deposition without a separate adhesion layer 210.

The electrode elements 215, 220, 225 can be located at varying positions and formed of many conductive materials. For example, the electrodes 215, 220, 225 can be fabricated using conductive materials, such as Gold or Aluminum. The center electrode element 220 can be proximate a center region of the substrate. The side electrode elements 215, 225 can be proximate side regions of the substrate 205 and the cMUT 200. The electrode elements 215, 220, 225 can also be located in different locations. The side electrode elements 215, 225 can be placed at a greater distance from the substrate 205 than the center electrode element 220. For example, the side electrode elements 215, 225 can be disposed within a dielectric layer 212, such as silicon nitride. The side electrode elements 215, 225 can also be located the same distance from the substrate 205 as the center electrode element 220 in some embodiments. The electrode elements 215, 220, 225 can be orientated substantially parallel to the substrate 205, or each can be orientated differently at varying orientations.

The cMUT 200 can further comprise an isolation layer 230. The isolation layer 230 can isolate the electrode elements 215, 220, 225 from each other physically, although at later steps of fabrication, the elements 215, 220, 225 can be electronically coupled. The isolation layer 230 can also enable the use of certain etchants to fabricate a cMUT that would otherwise harm or degrade unprotected electrode elements 215, 220, 225 or the substrate 205. The isolation layer 230 can comprise silicon nitride, or many other dielectric materials. In some embodiments the isolation layer 230 may not be utilized since certain etchants may not harm or degrade the electrode elements 215, 220, 225 or the substrate 205.

The cMUT 200 can also comprise a cavity 235 defined by a membrane 240. The cavity 235 can be formed by etching or removing a sacrificial layer proximate the isolation layer 230. The sacrificial layer preferably comprises Chromium. Other materials capable of being removed by etching procedures can also be used. The membrane 240 can be deposited on the sacrificial layer before the sacrificial layer is etched. The cavity 235 enables the membrane 240 to fluctuate and move relative to the substrate 205 in response to stimuli. The membrane 240 can comprise multiple layers of membrane materials, such as silicon nitride.

The cMUT 200 can also comprise a top electrode 245 disposed within the membrane 240. The top electrode 245 can be deposited on a first layer of membrane material and then a second layer of membrane material can be deposited on the top electrode 245, thus enveloping the top electrode 245 within the membrane 240. The top electrode 245 is preferably fabricated using a conductive material, such as Gold or Aluminum.

The cMUT 200 can be provided with signals from a first voltage source 260 ($V_1$) and a second voltage source 265 ($V_2$). A first voltage source 260 can provide a first voltage ($V_1$) between the side electrode elements 215, 225 and the top electrode 245, and a second voltage source 265 can provide a second voltage ($V_2$) between the center electrode element 220 and the top electrode 245. The side electrode elements 215, 225, although physically separated by a distance, can be electrically coupled so that a voltage or signal supplied to one of the electrode elements 215, 225 will be provided to the other of the electrode elements 215, 225. By providing these voltages at different time intervals, the cMUT 200 can be optimized for transmitting and receiving ultrasonic acoustic waves.

Additionally, these voltages ($V_1$, $V_2$) can enable the cMUT 200 to operate in a receiving state and a transmission state. Preferably, the first voltage source 260 ($V_1$) is adapted to provide a first voltage ($V_1$) between the side electrode elements 215, 225 and the top electrode 245 in both the transmission state and the receive state. And the second voltage source 265 ($V_2$) is preferably adapted to provide a second voltage ($V_2$) between the center electrode element 220 and the top electrode 245 in the receiving state. The side electrode elements 215, 225 can also receive ultrasonic acoustical waves, and the center electrode element 220 can also transmit ultrasonic energy, such as acoustic waves.

The cMUT 200 can be utilized to sense images. For example, the cMUT 200 can be adapted to receive a fluctuating capacitance between the electrode elements 215, 220, 225 and 245 in response to environmental factors (such as external applied pressures). The cMUT 200 can also be adapted to provide the fluctuating capacitance to a system that produces an image from the received capacitance. An integrated circuit 250 can sense signals produced by the fluctuation of the top electrode 245 relative to the side electrode elements 215, 225 and the center electrode element 220, and provide those electronic signals to an image processor 255. Those skilled in the art will be familiar with various methods for translating capacitance measurements on a cMUT imaging array into an image using an image processor 255 or similar system. The electrode elements 215, 225, 220, 245 can be coupled to an integrated circuit 250 through vias formed in the layers of the cMUT 200. The integrated circuit 250 can comprise CMOS electronic devices or other transistor-type devices.

Additionally, the cMUT 200 can be utilized to sense a variety of real-time information. For example, the device can be adapted to be a pressure sensor, a temperature sensor, a flow sensor, a Doppler flow sensor, an electrical resistivity sensor, a fluid viscosity sensor, a gas sensor, a chemical sensor, an accelerometer, or other desirable sensors. In addition, when used in imaging applications, the cMUT 200 can be a florescence or optical reflectivity sensor adapted to measure reflected and scattered light from surrounding tissue and fluids to monitor optical parameters such as reflectivity and fluorescence.

The cMUT 200 can be fabricated from a plurality of layers. Conductive materials can form conductive layers, which can be configured to form the electrode elements 215, 225, 220, 245. For example, the conductive material can be a doped silicon surface of the substrate 205, a doped polysilicon layer, a conductive metal, or other suitable conductive materials. The electrode elements 215, 225, 220, 245 can be coupled to signal generation and detection circuits such as the integrated electronic circuit 250. In some embodiments, the signal generation and detection circuits can be embedded within the substrate 205 or can be located on another chip proximate the substrate 205.

Figure 3:
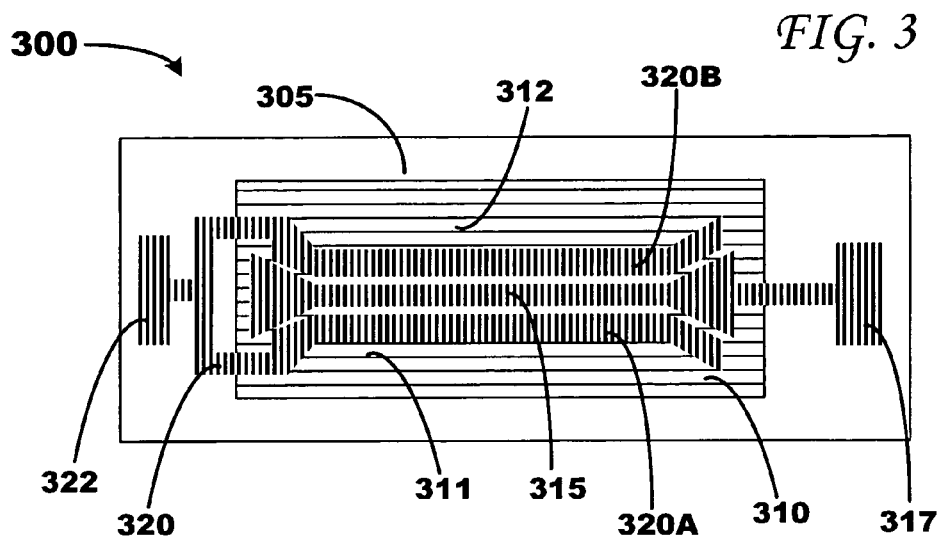
FIG. 3 illustrates a top view of a cMUT having a multi-element electrode in accordance with a preferred embodiment of the present invention.

FIG. 3 illustrates a top view of a cMUT 300 having a multi-element electrode in accordance with a preferred embodiment of the present invention. The cMUT 300 generally comprises a substrate 305, a membrane 310, a center electrode element 315, and a side electrode element pair 320.

More electrode elements can be used in other embodiments of the present invention. The center electrode element 315 and side electrode element pair 320 can be proximate the substrate 305 and can be partially disposed within the membrane 310. The membrane 310 can be proximate the substrate 305 and preferably defines a cavity, as illustrated in FIGS. 1 and 2. In addition, the membrane 310 can have side areas 311, 312 on either side of the membrane 310.

The center electrode element 315 and side electrode element pair 320 can have varying geometric shapes and locations within the membrane 310. As shown, the center electrode element 315 can be rectangular-shaped and centrally located within the membrane 310. The side electrode element pair 320 can be rectangular-shaped and, as shown, have side electrode elements 320A, 320B. The side electrode element pair 320 can also have more than two electrode elements in accordance with the present invention. The side electrode elements 320A, 320B can be substantially parallel to the center electrode element 315. The side electrode elements 320A, 320B of the side electrode element pair 320 can have a width less than that the center electrode 315, and can be located near sides areas 311, 312 of the membrane 310. The distance between the center electrode element 315 and the side electrode elements 320A, 320B can vary. This distance can aid in controlling the parasitic capacitance between the center electrode element 315 and the side electrode element pair 320 as the distance between the center electrode element 315 and the side electrode element pair 320 affects the capacitance between the electrode elements 315, 320.

The center electrode element 315 and side electrode element pair 320 can be adapted to receive and transmit ultrasonic acoustical waves. In some embodiments, the center electrode element 315 can be adapted to receive ultrasonic acoustical waves and the side electrode elements 320A, 320B can be adapted to transmit ultrasonic acoustical waves. The center electrode element 315 and the side electrode element pair 320 can be coupled to different voltage sources enabling them to optimally receive and transmit ultrasonic acoustical waves. For example, the center electrode element 315 can have a first bond pad area 317 and the side electrode element pair can have a second bond pad area 322 that each provide connection areas for coupling the center electrode element 315 and the side electrode element pair 320 to different voltage sources. Although it is preferable that one of the electrode elements 315, 320 act as receiving electrode elements and the other as a transmission electrode element, the electrode elements can act as a receiving electrode element and a transmission electrode element. The membrane 310 can fluctuate in response to signals and voltages applied to the electrode elements 315, 320.

Figure 4A:
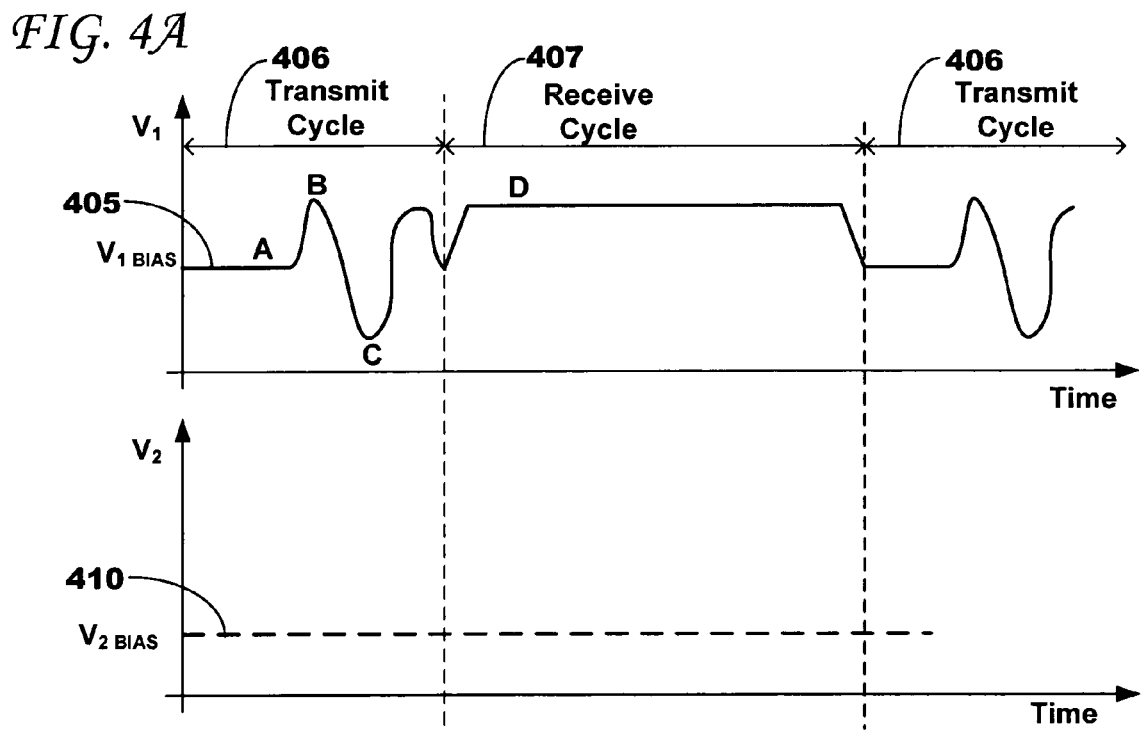
FIG. 4A illustrates a sample timing diagram of signals provided to a cMUT comprising a multi-element electrode in accordance with a preferred embodiment of the present invention.

FIG. 4A illustrates a sample timing diagram of signals provided to a cMUT comprising a multi-element electrode in accordance with a preferred embodiment of the present invention. Two different voltages can be used to place a cMUT having a multi-element electrode in a receiving state and a transmitting state. The voltages can be bias voltages as shown in FIG. 4A. For example, a first voltage source 160 ($V_1$) can provide an AC signal 405 to a transmit electrode element and a second voltage source 165 ($V_2$) can apply a DC voltage 410 to a receive electrode element. Applying the AC signal and a DC voltage to a cMUT can optimize the transmission and receiving operating states of a cMUT, as the voltages can be provided to electrodes to shape or adjust a membrane 420.

Multiple voltage sources ($V_1, V_2$) 160, 165 can provide the AC signal 405 and the bias voltage 410 to cMUT electrode elements, and the voltage sources 160, 165 can provide the signals simultaneously. Additionally, the voltage sources 160, 165 can be adapted to provide the AC signal 405 and the bias voltage 410 during a transmit cycle 406 and a receive cycle 407. During a transmit cycle 406, a cMUT can be optimized for transmitting an acoustic wave, and during a receive cycle 407, a cMUT can be optimized for receiving an acoustic wave. The AC signal 405 can rise to a positive peak at B from a base level A, fall to a negative peak at C, rise to a positive peak at C, and eventually rise to a constant level D approximately equal to the positive peak at B during a transmit cycle 406 and a receive cycle 407. The bias voltage 410 can remain substantially constant during the transmit and receive cycles 406, 407. The level of the bias voltage 410 can be close to the membrane collapse voltage such that while in the receive cycle 406, the membrane is close to collapsing. During a receive cycle 407, the AC signal 405 and the DC voltage 410 can remain substantially constant to shape the membrane 420 for optimal reception.

Figure 4B:
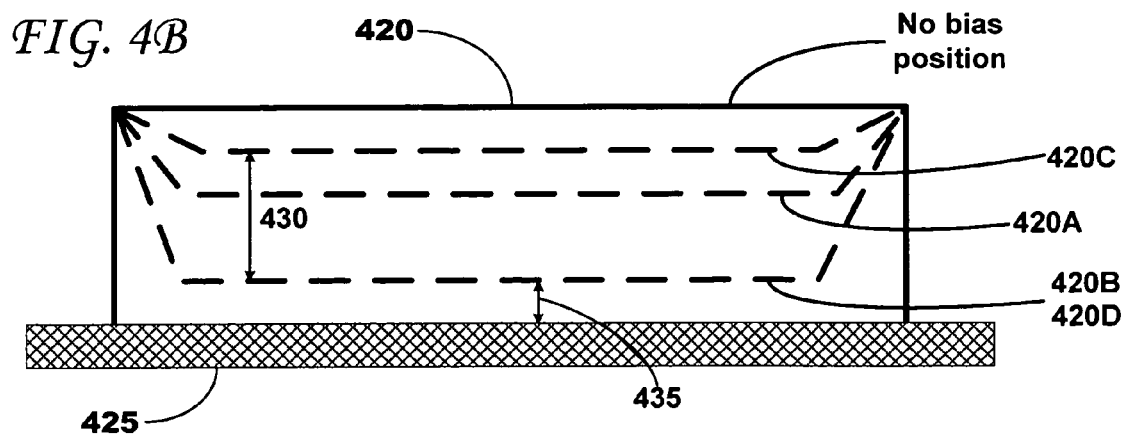
FIG. 4B illustrates cMUT membrane shapes achieved in response to the signals illustrated in FIG. 4A being provided to a cMUT in accordance with a preferred embodiment of the present invention.

FIG. 4B illustrates a cMUT membrane 420 fluctuating in response to the signals 405, 410 illustrated in FIG. 4A provided to a cMUT in accordance with a preferred embodiment of the present invention. When a cMUT membrane 420 is not biased with a bias voltage, (electrically neutral) it can be substantially horizontal or planar. Upon the initiation of a transmit cycle 406 and at A, the membrane 420 is biased (pulled) toward a substrate 425 (see 420A). At B, during the transmit cycle 406, the membrane 420 is biased toward the substrate 425, such that the membrane 420 is close to collapsing and contacting the substrate 425 (see 420B). At C, during the transmit cycle 406, the membrane 420 can rebound toward the no bias position (see 420C). As shown, the membrane 420 can have a relatively large fluctuation 430 between 420B and 420C during a transmit cycle 406.

Upon the initiation of a receive cycle 407 and at D, the membrane 420 can be biased so that the membrane 420 moves toward a substrate 425 (see 420D). As shown in FIG. 4B, the membrane 420 can be close to the substrate 405 creating a relatively small gap 435 during the receive cycle. For multiple transmit/receive cycles, the voltage sources can continuously provide the AC signal 405 and the DC voltage 410 to aid in shaping the membrane 420 for transmitting and receiving acoustic ultrasonic waves.

Figure 5:
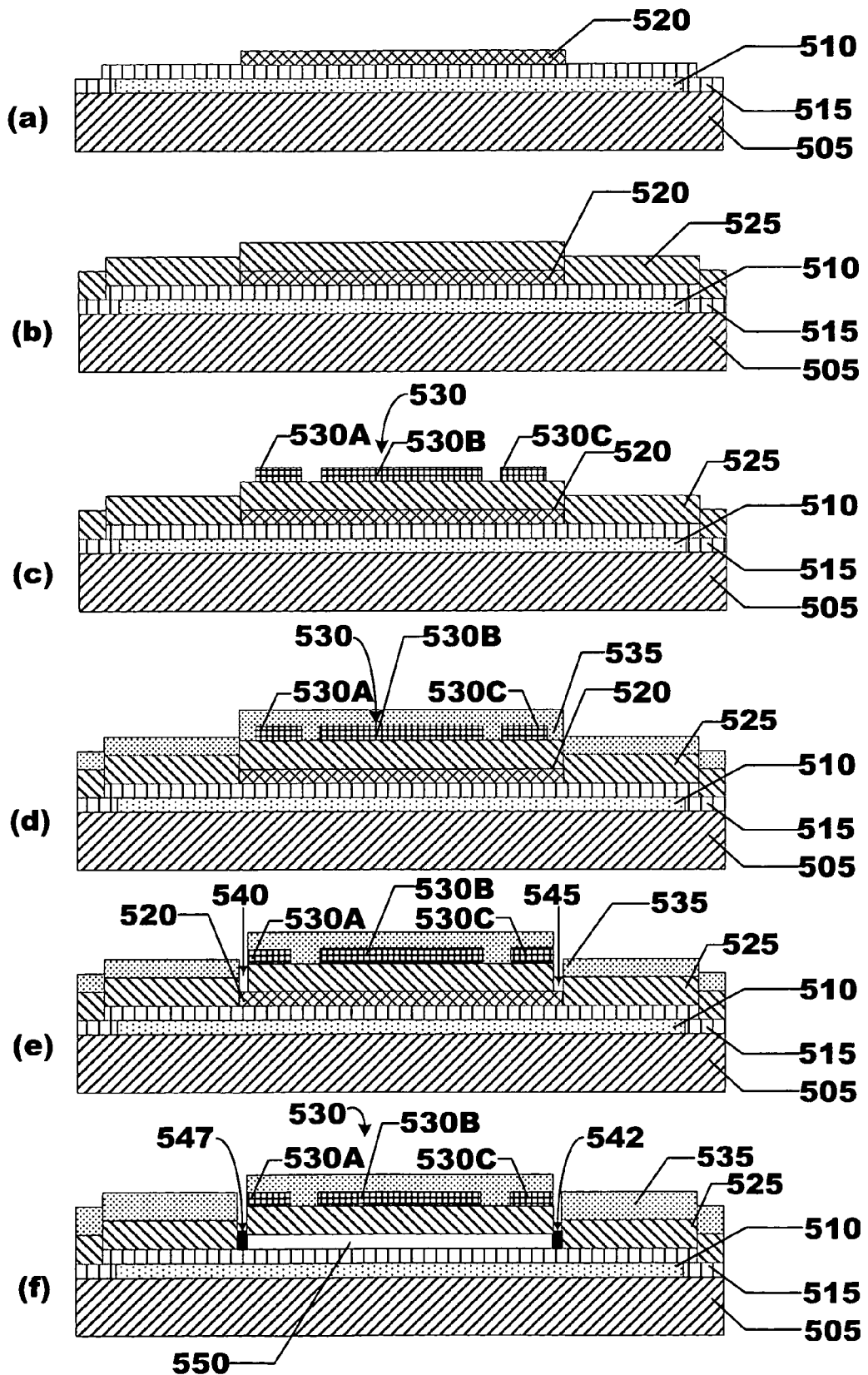
FIG. 5 illustrates a fabrication process utilized to fabricate a cMUT comprising a multi-element electrode in accordance with a preferred embodiment of the present invention.

FIG. 5 illustrates a fabrication process utilized to fabricate a cMUT comprising a multi-element electrode in accordance with a preferred embodiment of the present invention. Typically, the fabrication process is a build-up process that involves depositing various layers of materials on a substrate 505, and patterning the various layers in predetermined configurations to fabricate a cMUT on the substrate 505.

In a preferred embodiment of the present invention, a photoresist such as Shipley S-1813 is used to lithographically define various layers of a cMUT. Such a photoresist material does not require the conventional use of high temperatures for patterning vias and material layers. Alternatively, many other photoresist or lithographic materials can be used.

A first step in the present fabrication process provides a bottom electrode 510 on a substrate 505. The substrate 505 can comprise dielectric materials, such as silicon, quartz, glass, or sapphire. In some embodiments, the substrate 505 contains integrated electronics 150, and the integrated electronics can be separated for transmitting and receiving signals. Alternatively, a second substrate (not shown) located proximate the substrate 505 containing suitable signal transmission and detection electronics can be used. A conductive material, such as conductive metals, can form the bottom electrode 510. The bottom electrode 510 can also be formed by doping a silicon substrate 505 or by depositing and patterning a conductive material layer (such as metal) on the substrate 505. Yet, with a doped silicon bottom electrode 510, all non-moving parts of a top electrode can increase parasitic capacitance, thus degrading device performance and prohibiting optical detection techniques for most of the optical spectrum.

To overcome these disadvantages, a patterned bottom electrode 510 can be used. As shown in FIG. 5(a), the bottom electrode 510 can be patterned to have a different length than the substrate 505. By patterning the bottom electrode 510, device parasitic capacitance can be significantly reduced.

The bottom electrode 510 can be patterned into multiple electrode elements, and the multiple electrode elements can be located at varying distances from the substrate 505. Aluminum, chromium, and gold are exemplary metals that can be used to form the bottom electrode 510. In one preferred embodiment of the present invention, the bottom electrode 510 has a thickness of approximately 1500 Angstroms, and after deposition, can be patterned as a diffraction grading, and/or to have various lengths.

In a next step, an isolation layer 515 is deposited. The isolation layer 515 can isolate portions of or the entire bottom electrode 510 from other layers placed on the bottom electrode 510. The isolation layer 515 can be silicon nitride, and preferably has a thickness of approximately 1500 Angstroms. A Unaxis 790 PECVD system can be used to deposit the isolation layer 515 at approximately 250 degrees Celsius in accordance with a preferred embodiment. The isolation layer 515 can aid in protecting the bottom electrode 510 or the substrate 505 from etchants used during cMUT fabrication. Once deposited onto the bottom electrode layer 510, the isolation layer 515 can be patterned to a predetermined thickness. In an alternative preferred embodiment, an isolation layer 515 is not utilized.

After the isolation layer 515 is deposited, a sacrificial layer 520 is deposited onto the isolation layer 515. The sacrificial layer 520 is preferably only a temporary layer, and is etched away during fabrication. When an isolation layer 515 is not used, the sacrificial layer 520 can be deposited directly on the bottom electrode 510. The sacrificial layer 520 is used to hold a space while additional layers are deposited during cMUT fabrication. The sacrificial layer 520 can be used to help create a chamber, such as a cavity or a via during fabrication. The sacrificial layer 520 can be formed with amorphous silicon that can be deposited using a Unaxis 790 PECVD system at approximately 300 degrees Celsius and patterned with a reactive ion etch ("RIE"). Sputtered metal can also be used to form the sacrificial layer 520. The sacrificial layer 520 can be patterned into different sections, various lengths, and different thicknesses to provide varying geometrical configurations for a resulting cavity or via.

A first membrane layer 525 is then deposited onto the sacrificial layer 520, as shown in FIG. 5(b). For example, the first membrane layer 525 can be deposited using a Unaxis 790 PECVD system. The first membrane layer 525 can be a layer of silicon nitride or amorphous silicon, and can be patterned to have a thickness of approximately 6000 Angstroms. The thickness of the first membrane layer 525 can vary depending on the particular implementation. Depositing the first membrane layer 525 over the sacrificial layer 520 aids in forming a vibrating cMUT membrane.

After patterning the first membrane layer 525, a second conductive layer 530 can be deposited onto the first membrane layer 525 as illustrated in FIG. 5(c). The second conductive layer 530 can form the top electrode(s) of a cMUT. The second conductive layer can be patterned into different electrode elements 530A, 530B, 530C that can be separate elements from each other. One or more of the electrode elements 530A, 530B, 530C can be electrically coupled forming an electrode element pair. The electrodes 530A, 530B, 530C can be placed at varying distances from the substrate 505. As shown in FIG. 5(d), the second conductive layer 530 can be patterned into a first electrode element 530A and a second electrode element 530B. The first electrode element 530A can be coupled to a third electrode element 530C, forming an electrode element pair. Preferably, the formed electrode pair 530A, 530C is electrically isolated from the second electrode element 530B.

The electrode element pair 530A, 530C can be formed from conductive metals such as Aluminum, Chromium, Gold, or combinations thereof. In an exemplary embodiment, the electrode element pair 530A, 530C comprises Aluminum having a thickness of approximately 1200 Angstroms and Chromium having a thickness of approximately 300 Angstroms. Aluminum provides good electrical conductivity, and Chromium can aid in smoothing any oxidation formed on the Aluminum during deposition. Additionally, the electrode element pair 530A, 530C can comprise the same conductive material or a different conductive material than the first conductive layer 510.

In a next step, a second membrane layer 535 is deposited over the electrode elements 530A, 530B, 530C as illustrated in FIG. 5(d). The second membrane layer 535 increases the thickness of the cMUT membrane at this point in fabrication (formed by the first and second membrane layers 525, 535), and can serve to protect the second conductive layer 530 from etchants used during cMUT fabrication. The second membrane layer 535 can also aid in isolating the first electrode element 530A from the second electrode element 530B. The second membrane layer can be approximately 6000 Angstroms thick. In some embodiments, the second membrane layer 535 is adjusted using deposition and patterning techniques so that the second membrane layer 535 has an optimal geometrical configuration. Preferably, once the second membrane layer 535 is adjusted according to a predetermined geometric configuration, the sacrificial layer 520 is etched away, leaving a cavity 550 as shown in FIG. 5(f).

To enable etchants to reach the sacrificial layer 520, apertures 540, 545 can be etched through the first and second membrane layers 525, 535 using an RIE process. As shown in FIG. 5(e), access passages to the sacrificial layer 520 can be formed at apertures 540, 545 by etching away the first and second membrane layers 525, 535. When an amorphous silicon sacrificial layer 520 is used, one must be aware of the selectivity of the etch process to silicon. If the etching process has low selectivity, one can easily etch through the sacrificial layer 520, the isolation layer 515, and down to the substrate 505. If this occurs, the etchant can attack the substrate 505 and can destroy a cMUT device. When the bottom electrode 510 is formed from a metal that is resistant to the etchant used with the sacrificial layer, the metal layer can act as an etch retardant and protect the substrate 505. After the sacrificial layer 520 is etched, the cavity 550 can be sealed with seals 542, 547, as shown in FIG. 5(f).

The cavity 550 can be formed between the isolation layer 515 and the membrane layers 525, 535. The cavity 550 can also be disposed between the bottom conductive layer 510 and the first membrane layer 525. The cavity 550 can be formed to have a predetermined height in accordance with some preferred embodiments of the present invention. The cavity 550 enables the cMUT membrane, formed by the first and second membrane layers 525, 535, to fluctuate and resonate in response to stimuli. After the cavity 550 is formed by etching the sacrificial layer 520, the cavity 550 can be vacuum sealed by depositing a sealing layer (not shown) on the second membrane layer 535. Those skilled in the art will be familiar with various methods for setting a pressure in the cavity 550 and then sealing it to form a vacuum seal.

The sealing layer is typically a layer of silicon nitride, having a thickness greater than the height of the cavity 550. In an exemplary embodiment, the sealing layer has a thickness of approximately 4500 Angstroms, and the height of the cavity 550 is approximately 1500 Angstroms. In alternative embodiments, the second membrane layer 535 is sealed using a local sealing technique or sealed under predetermined pressurized conditions. Sealing the second membrane layer 535 can adapt the cMUT for immersion applications. After depositing the sealing layer, the thickness of the composite cMUT membrane can be adjusted by etching back the sealing layer since the cMUT membrane may be too thick to resonate at a desired frequency. A dry etching process, such as RIE, can be used to etch the sealing layer.

A final step in the present cMUT fabrication process prepares the cMUT for electrical connectivity. Specifically, RIE etching can be used to etch through the isolation layer 515 on the bottom electrode 510, and the second membrane layer 535 on the top electrode 530 making the electrodes 510, 530 accessible.

Additional bond pads can be formed and connected to the electrode. Bond pads enable external electrical connections to be made to the top and bottom electrodes 510, 530 with wire bonding. In some embodiments, gold can be deposited and patterned on the bond pads to improve the reliability of the wire bonds.

In an alternative embodiment of the present invention, the sacrificial layer 520 can be etched after depositing the first membrane layer 525. This alternative embodiment invests little time in the cMUT device before performing the step of etching the sacrificial layer 520 and releasing the membrane formed by the membrane layers. Since the top electrode 530 has not yet been deposited, there is no risk that pinholes in the second membrane layer 535 could allow the top electrode 530 to be destroyed by etchants.

Figure 6:
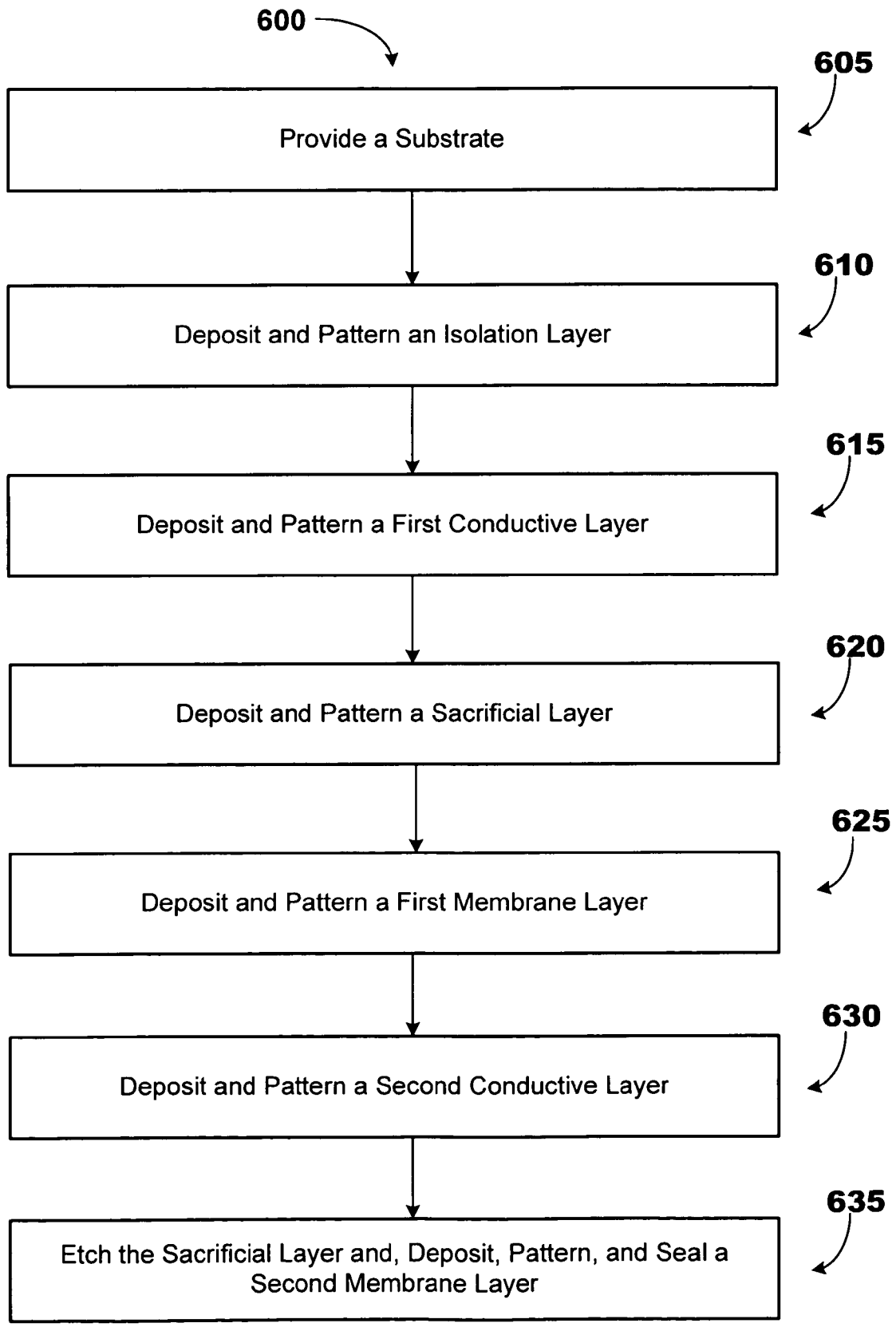
FIG. 6 illustrates a logical flow diagram depicting a fabrication process utilized to fabricate a cMUT comprising a multi-element electrode in accordance with a preferred embodiment of the present invention.

FIG. 6 illustrates a logical flow diagram depicting a preferred method to fabricate a cMUT comprising a multi-element electrode. The first step involves providing a substrate (605). The substrate can be an opaque, translucent, or transparent substrate. For example, the substrate can be formed of silicon, glass, or sapphire. Next, an isolation layer is deposited onto the substrate, and patterned to have a predetermined thickness (610). The isolation layer is optional, and may not be utilized in some embodiments. An adhesive layer can also be used in some embodiments ensuring that an isolation layer bonds to a substrate.

After the isolation layer is patterned, a first conductive layer is deposited onto the isolation layer, and patterned into a predetermined configuration (615). Alternatively, a doped surface of a substrate, such as a doped silicon substrate surface, can form the first conductive layer. The first conductive layer preferably forms a bottom electrode for a cMUT on a substrate. The first conductive layer can be patterned to form multiple electrodes. At least two of the multiple electrodes can be coupled together to form an electrode having multiple electrode elements.

Once the first conductive layer is patterned into a predetermined configuration, a sacrificial layer can be deposited onto the first conductive layer (620). The sacrificial layer is patterned by selective deposition and patterning techniques so that it has a predetermined thickness. Then, a first membrane layer can be deposited onto the sacrificial layer (625).

The deposited first membrane layer is then patterned to have a predetermined thickness, and a second conductive layer is then deposited onto the first membrane layer (630). The second conductive layer preferably forms a top electrode for a cMUT. The second conductive layer can be patterned to form multiple electrode elements. At least two of the multiple electrode elements can be coupled together to form an electrode element pair. After the second conductive layer is patterned into a predetermined configuration, a second membrane layer is deposited onto the patterned second conductive layer (635). The second membrane layer can also be patterned to have an optimal geometric configuration.

The first and second membrane layers can encapsulate the second conductive layer, enabling it to move relative to the first conductive layer due to elastic characteristics of the first and second membrane layers. After the second membrane layer is patterned, the sacrificial layer is etched away, forming a cavity between the first and second conductive layers (635). The cavity formed below the first and second membrane layers provides space for the resonating first and second membrane layers to move relative to the substrate. In a last part of this step, the second membrane layer is sealed by depositing a sealing layer onto the second membrane layer (635).

The embodiments of the present invention can also be utilized to form a cMUT array for a cMUT imaging system. The cMUT imaging arrays illustrated in FIGS. 7 and 8 are only exemplary, as other imaging arrays are achievable in accordance with the embodiments of the present invention.

Figure 7:
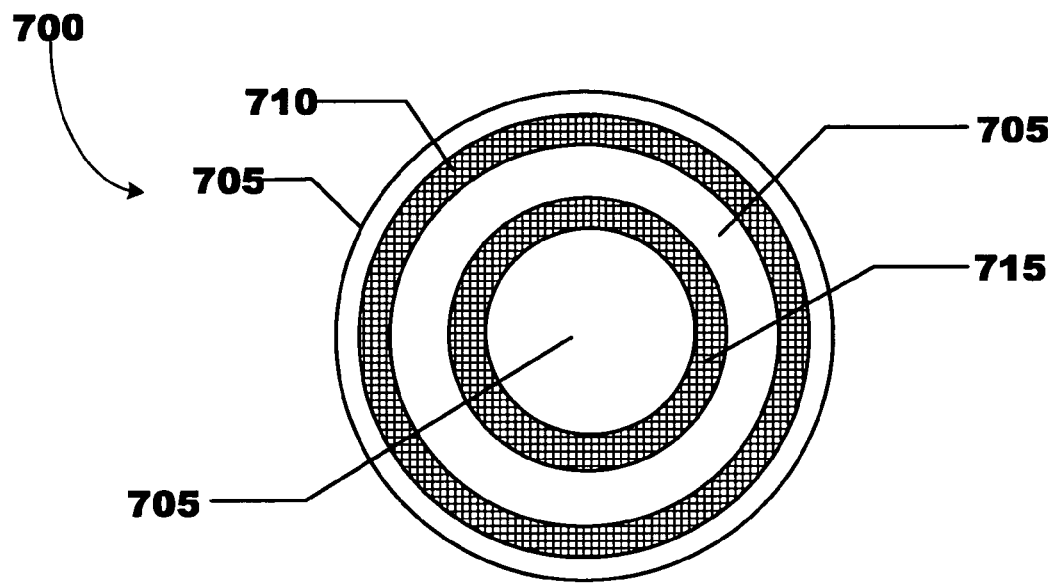
FIG. 7 illustrates a cMUT imaging array system comprising multiple multi-element-electrode cMUTs formed in a ring-annular array in accordance with a preferred embodiment of the present invention.

FIG. 7 illustrates a cMUT imaging array device formed in a ring-annular array on a substrate. As shown, the device 700 includes a substrate 705 and cMUT arrays 710, 715. The substrate 705 is preferably disc-shaped, and the device 700 can be utilized as a forward looking cMUT imaging array. Although the device 700 is illustrated with two cMUT arrays 710, 715, other embodiments can have one or more cMUT arrays. If one cMUT array is utilized, it can be placed near the outer periphery of the substrate 705. If multiple cMUT arrays are utilized, they can be formed concentrically so that the circular-shaped cMUT arrays have a common center point. Some embodiments can also utilize cMUT arrays having different geometrical configurations in accordance with some embodiments of the present invention.

Figure 8:
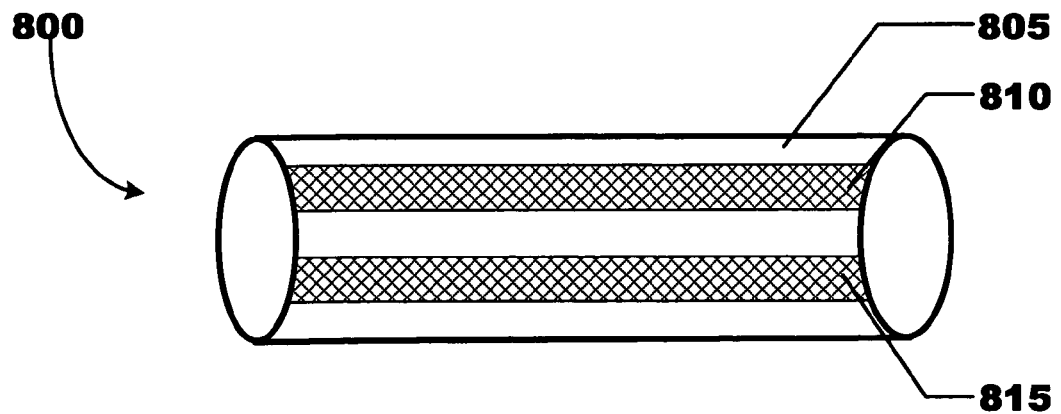
FIG. 8 illustrates a cMUT imaging array system comprising multiple multi-element-electrode cMUTs formed in a side-looking array in accordance with a preferred embodiment of the present invention.

FIG. 8 illustrates a cMUT imaging array system formed in a side-looking array on a substrate. As shown, the device 800 includes a substrate 805, and cMUT arrays 810, 815. The substrate 805 can be cylindrically-shaped, and the cMUT arrays can be coupled to the outer surface of the substrate 805. The cMUT arrays 810, 815 can comprise cMUT devices arranged in an interdigital fashion and used for a side-looking cMUT imaging array. Some embodiments of device 800 can include one or multiple cMUT imaging arrays 810, 815 in spaced apart relation on the outer surface of the cylindrically-shaped substrate 800.

In another preferred embodiment of the present invention, the components of the cMUT can be fabricated according to a predetermined geometric configuration. A preferred embodiment of the present invention is described with particular dimensions, but those skilled in the art will recognize that these dimensions are merely examples and are not intended to limit the scope of the present invention. For convenience, the components of the cMUT in this preferred embodiment will be discussed with reference to FIG. 1. However, the description of particular functions of the components or specific arrangement and sizes of the components are not intended to limit the scope of FIG. 1 and are provided only for example, and not limitation.

In a preferred embodiment, a 0.3 mm by 0.65 mm rectangular cMUT 100 incorporating 20 μm wide by 100 μm long by 0.9 μm thick rectangular silicon nitride membranes 130 is fabricated. The transmit electrodes 135, 145 are 4 μm wide and located at the edges of the membrane 130, and an 8 μm wide receive electrode 140 is located near the center of the membrane 130. Experimental results using this structure yielded a 6.8 dB increase in maximum output pressure at 9 MHz with side electrode excitation over standard single electrode transmission.

A second advantage of a dual electrode structure is the reduction of the dead zone during pulse echo operation. Since the DC bias of the electrode elements can be controlled independently, the receive electrode element 140 can be biased to near collapse immediately after transmission for optimized receive operation. Additionally, separate electronics can be used for transmit and receive without the need for a switch. Simulations showed that the parasitic capacitance introduced by the transmit electrode elements 135, 145 is negligible and should not cause any degradation in the receive performance.

The positioning of the transmit electrode elements 135, 145 at the sides of the membrane 130 make use of the effect know as "leveraged bending" to increase the stable range of motion of the membrane 130. Leveraged bending increases the range of travel of electrostatically actuated MEMS devices to nearly the full cavity 125, as opposed to the typical displacement of one third of the cavity 125. By increasing the range of motion of the membrane 130, the volume displacement can be increased, thereby increasing the transmit pressure.

In addition to increasing the transmit pressure, the multiple electrode elements 135, 140, 145 allow the transmit and receive electronics to be separated and limits or even eliminates the need for problematic switches. This decoupling of transmit and receive electronics has the potential to decrease the dead-zone in ultrasonic images by decreasing the ringing in the amplifiers.

Figure 9:
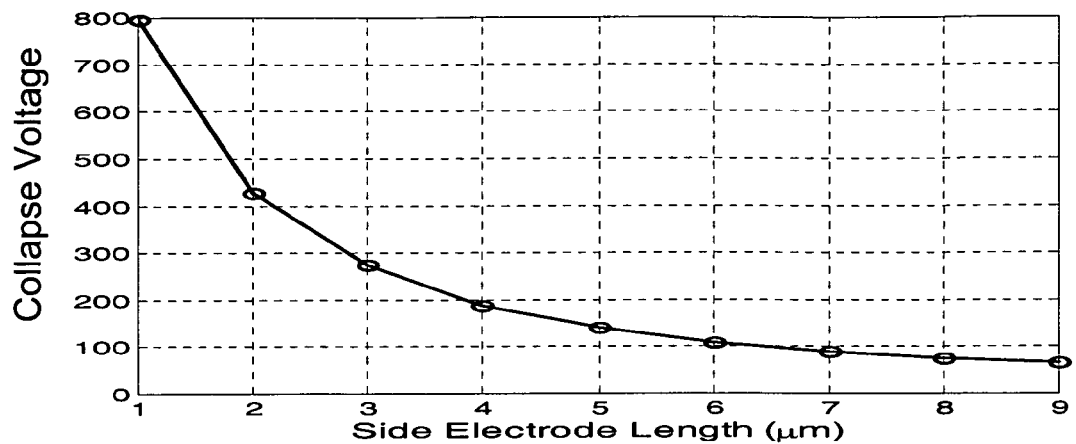
FIG. 9 illustrates a diagram of the collapse voltage for a sample cMUT membrane as a function of side electrode length.

A coupled field electrostatic analysis was performed on a preferred embodiment in ANSYS to determine the collapse voltage, displacement profile, and crosstalk capacitance of the devices. A 20 μm wide, 0.9 μm thick membrane 130 was simulated. The collapse voltage was determined as a function of the length of side electrode elements 135, 145 to determine the practical electrode element dimensions and locations. As expected, the collapse voltage was found to decrease as the length of the side electrode elements 135, 145 was increased. A plot of this behavior for a 20 μm wide membrane is shown in FIG. 9. As shown in FIG. 9, a side electrode element 135, 145 of length 4 μm yields a collapse voltage less than 200V.

Figure 10:
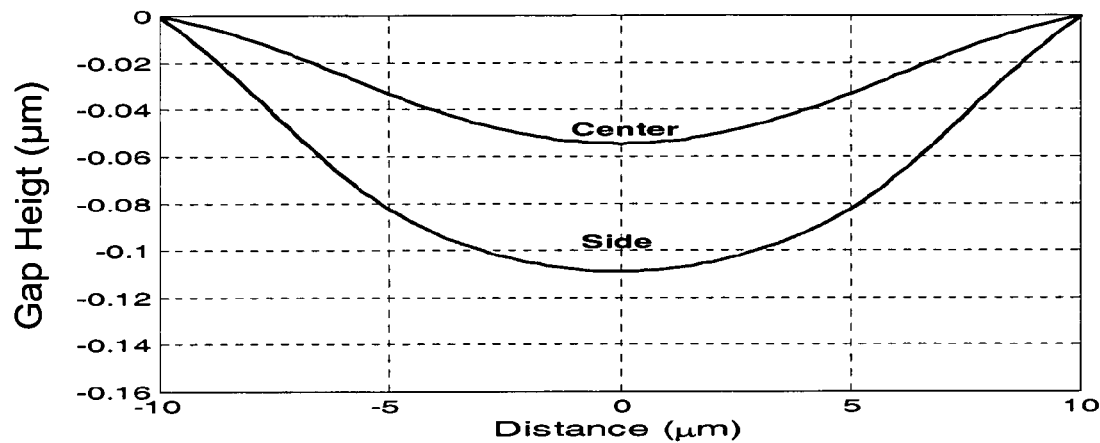
FIG. 10 illustrates a diagram of a sample membrane profile before membrane collapse.

FIG. 10 illustrated the results of an electrostatic simulation of a membrane profile just before collapse. As shown in FIG. 10, when the device is excited with the center electrode element 140, the membrane 130 collapses at approximately one third of the cavity 125 as expected. Additionally, under side electrode element 135, 145 excitation, the membrane 130 displacement before collapse has increased to nearly two thirds of the cavity 125 and the profile has a larger volume displacement than for center electrode element 140 excitation. For a device in accordance with this preferred embodiment, side electrode element excitation increases the volume displacement of the membrane 130 by a factor of approximately 2.3 over a single electrode element design. This indicates that the pressure output of a transducer under side electrode element excitation should be higher than traditional single electrode excitation.

Experiments were performed using a cMUT 100 fabricated in accordance with a preferred embodiment of the present invention. These experimental results are not intended to be limiting but are intended to aid in the understanding of the operation of embodiments of the present invention. The experimental results presented were obtained using a cMUT with an 8 μm center electrode element and 4 μm side electrode elements on a 20 μm wide, 0.9 μm thick silicon nitride membrane. The multi-element element cMUT was first tested in a water tank to determine the shape of the transmit frequency spectrum.

Each electrode element of the cMUT was biased to 60V and then excited with an 8 ns, 20V peak pulse. This voltage pulse applied to the center electrode element generated an acoustic pulse in the water which was then recorded with a hydrophone. After recording the waveform for the center electrode element, the electrical connections were switched to test the side electrode elements. The resulting frequency spectra of the received signals under center and side electrode elements are shown in FIG. 11.

Figure 11:
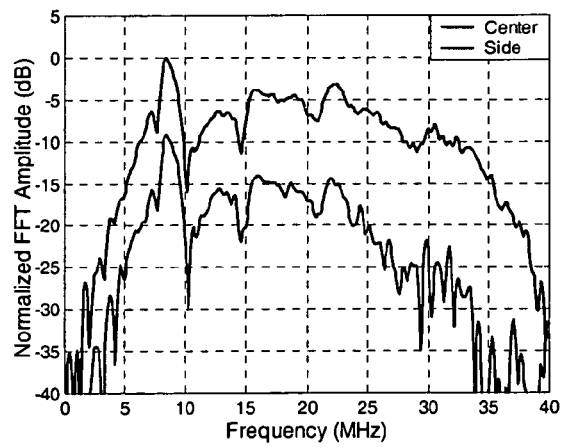
FIG. 11 illustrates a diagram of frequency spectra for a sample cMUT having center and side electrode element excitation in accordance with a preferred embodiment of the present invention.

As shown in FIG. 11, the spectra are broad-band with a strong resonance at approximately 10 MHz. This resonance is expected since the cMUT membrane was originally designed to generate an acoustic crosstalk mode at 10 MHz. One can also observe that for the same DC bias, the spectrum of the side electrode elements is approximately 10 dB less than that for the center electrode element. This was confirmed using a simple acoustic finite element model. The gains in transmit pressure result from the application of larger swing voltages to the side electrode elements than are possible with the center electrode element.

After determining the transmit frequency response, the cMUT was excited with a tone burst at 9 MHz and a fixed DC bias. The DC bias was set to half of the collapse voltage for either the center or side electrode elements so that the maximum AC, or swing, voltage could be applied. Therefore, the bias was set to 60V for the center electrode element 140 and 120V for the side electrode elements. The amplitude of the received signal at the hydrophone was recorded as the swing voltage was varied and the resulting data is plotted in FIG. 12.

Figure 12:
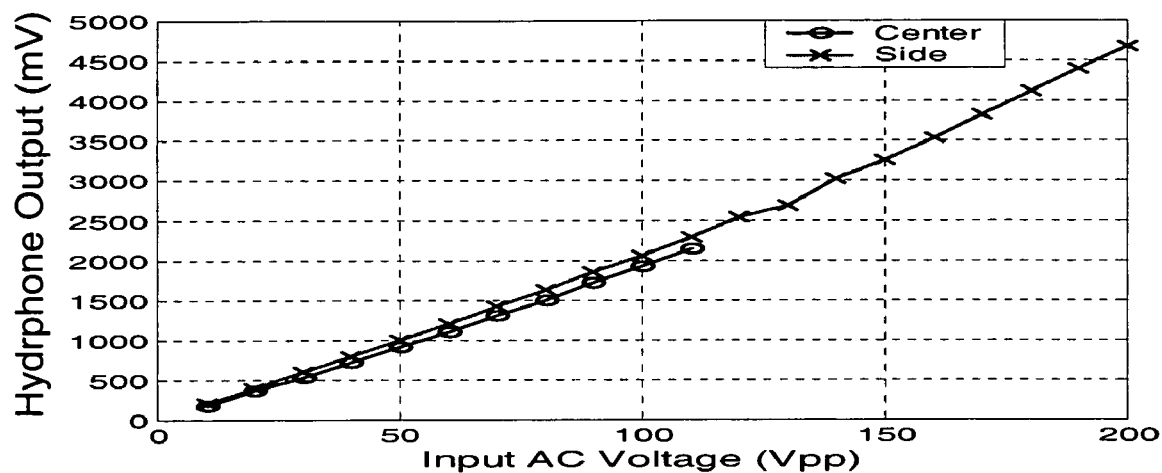
FIG. 12 illustrates a diagram of a diagram of a hydrophone output signal's amplitude as a function of input swing voltage for a sample cMUT in accordance with a preferred embodiment of the present invention.

As shown in FIG. 12, one can see that the transmit pressure is 6.8 dB higher under side electrode element excitation than under center electrode element excitation. This comes at the expense of higher DC bias voltages which can be reduced by moving the electrode elements closer to the substrate. Those skilled in the art will recognize that the area of the center electrode element was equal to that of the side electrode elements. Alternatively, the electrode elements can be alternative dimensions to achieve desired characteristics.

The Fourier transform of the received tone burst was calculated for signals resulting from center and side electrode element excitation. The AC amplitude was adjusted so that the pressure output side electrode element excitation was equal to the maximum pressure output under center electrode element excitation. The spectra indicate that side electrode element excitation generates 4 dB less of the second harmonic. This is expected since the cMUT operates far from collapse under side electrode element excitation.

A pulse-echo experiment was performed using the center electrode element and then the side electrode elements. An aluminum reflector was placed 1.5 mm from the substrate and the gap was filled with water. The electrode elements were biased to 90V and then excited with an 8 ns, 16V peak pulse. The reflected waveform was amplified and then recorded. The frequency spectra for center electrode element and side electrode element excitation are shown in FIG. 13.

Figure 13:
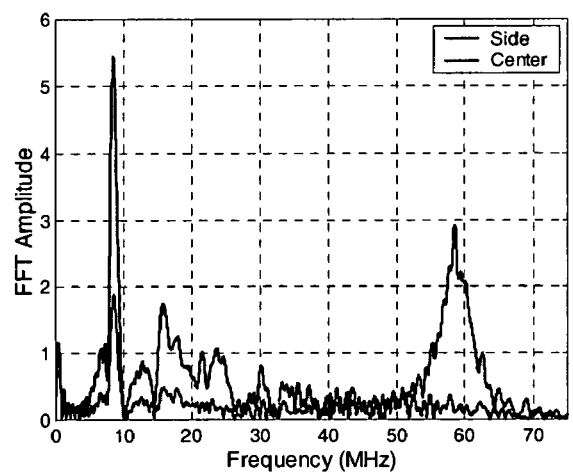
FIG. 13 illustrates a diagram of frequency spectra for a sample cMUT having center and side electrode element excitation in a pulse-echo experiment.

As shown in FIG. 13, the spectra for center electrode element and side electrode element excitation have a similar shapes for frequencies up to 35 MHz. However, in the range of 50 to 70 MHz, the frequency spectra are quite different. The curve for side electrode element excitation exhibits a large peak at approximately 58 MHz, which corresponds to the second resonant mode of the 20 μm wide membrane. This behavior compares well with a simple acoustic finite element model.

While the various embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all applicable equivalents.

I claim:

1. A cMUT comprising:
a multi-element electrode having at least a first electrode element and a second electrode element, the first and second electrode elements being spaced apart from each, forming part of different circuits, and operatively configured to transmit or receive an ultrasonic wave separately from each other such that the first electrode element can transmit or receive an ultrasonic wave separately from the second electrode element receiving or transmitting an ultrasonic wave; and
a membrane, the second electrode element being disposed proximate a central region of the membrane such that the second electrode element is positioned to actuate the central region of the membrane, the first electrode element being disposed generally between an edge region of the membrane and the central region to actuate a region intermediate the edge region and the central region, and the first electrode element and the second electrode element having cross-sectional widths less than the cross-sectional width of the membrane.

2. The cMUT of claim 1, wherein at least one of the first electrode element and the second electrode element is a hot electrode of the cMUT.

3. The cMUT of claim 1, wherein the first and second electrode elements are disposed within the membrane in at least one of a substantially co-planar arrangement or non-planar arrangement.

4. The cMUT of claim 1, wherein the first and second electrode elements are proximate a substrate.

5. The cMUT of claim 1 further comprising a third electrode element coupled to the first electrode element to form an electrode element pair, the electrode element pair being spaced apart from sides of the second electrode element such that the electrode element pair and the second electrode element can separately receive or transmit an ultrasonic wave and is electrically isolated from the second electrode element.

6. The cMUT of claim 1 further comprising a membrane shaping means to shape the membrane for reception or transmission of an ultrasonic wave, the membrane shaping means including at least one of the first electrode element and the second electrode element.

7. The cMUT of claim 1, the multi-element electrode further comprising a third electrode element, the third electrode element being disposed in an opposing position from the first electrode element such that the third electrode element is located generally between the central region of the membrane and a second edge region of the membrane to actuate a region of the membrane intermediate the second edge region and the central region.

8. The cMUT of claim 1, wherein the first electrode element and the second electrode element are a side electrode element pair adapted to cooperatively shape the membrane during transmission or receipt of an ultrasonic signal.

9. The cMUT of claim 1, the cMUT further comprising a bottom electrode and an electrode element pair, the electrode element pair comprising the first electrode element and a third electrode element,
the membrane and the bottom electrode being separated by a gap distance in an electrically neutral state, and the electrode element pair being operatively configured to flex at least a portion of the membrane by more than one third of the gap distance during transmission of an ultrasonic wave.

10. The cMUT of claim 1, further comprising a third electrode element and a side electrode element pair that comprises the first electrode element and the third electrode element,
the side electrode element pair being transmit elements, the second electrode element being a receive element, and the first and third electrode elements of the side electrode element pair each being so located at respective, opposing sides of the cMUT to make use of leveraged bending by flexing one or more regions of the membrane.

11. The cMUT of claim 6, the membrane shaping means being operatively configured to shape the membrane and not receive or transmit ultrasonic waves when shaping the membrane.

12. A method of transceiving ultrasonic waves comprising:
providing a cMUT having a membrane and a multi-element first electrode comprising a first electrode element and a second electrode element, both having cross-sectional widths less than the cross-sectional width of the membrane;
providing the first electrode element proximate a first portion of the cMUT membrane such that the first electrode element can actuate the first portion of the cMUT membrane;
providing the second element electrode proximate a second portion of the cMUT membrane such that the second electrode element can actuate the second portion of the cMUT membrane; and
adapting the cMUT to receive applying a first voltage at the first electrode element and a second voltage at the second electrode element such that the first electrode element and the second electrode element transmit an ultrasonic wave separate from each other.

13. The method of claim 12, further comprising adapting the cMUT to receive a bias voltage at least one of the first electrode element and the second electrode element for shaping the membrane to receive or transmit an ultrasonic wave signal.

14. The method of claim 13, further comprising adapting the cMUT to optically sense the received ultrasonic wave signal.

15. The method of claim 13, further comprising adapting the cMUT to electrically sense the received ultrasonic wave signal.

16. A method of fabricating a cMUT array comprising one or more cMUTs, the method comprising:
providing a top conductor;
providing a bottom conductor separated by a gap distance from the top conductor;
configuring at least one of the top and bottom conductors into a plurality of electrode elements such that a number of the electrode elements can transmit and receive ultrasonic waves separate from another number of the electrode elements receiving or transmitting ultrasonic waves;

configuring at least one of the plurality of electrode elements into at least a set of three conductors for each cMUT, the set of three conductors comprising a first electrode element, a second electrode element, and a third electrode element each having a cross-sectional width less than the cross-sectional width of the cMUT;

providing the first and the third electrode elements proximate opposing cross-sectional width portions of the cMUT such that the first and third electrode elements can actuate opposing cross-sectional width portions of the cMUT; and providing the second electrode element intermediate the first and second electrode elements such that ends of the second electrode element are spaced apart from opposing ends of the first and third electrode elements.

17. The method of claim 16, further comprising configuring the top and bottom conductors to be electrically coupled to a voltage source.

18. The method of claim 16, further comprising:
adapting the first and the third electrode elements to receive a first voltage to shape at least one of the opposing cross-sectional width ends of the cMUT for receiving or transmitting ultrasonic waves; and
adapting the second electrode element to receive a second voltage to shape a membrane region of the cMUT intermediate the opposing cross-sectional width ends of the cMUT.

19. The method of claim 16, further comprising:
providing a sacrificial layer proximate the bottom conductor;
providing a first membrane layer proximate the sacrificial layer;
providing a second membrane layer proximate the top conductor; and
removing the sacrificial layer.

20. The method of claim 19, further comprising disposing the top conductor between the first membrane layer and the second membrane layer.

21. The method of claim 16, further comprising electrically coupling at least two of the electrode elements of the plurality of electrode elements.

22. A cMUT for use with ultrasonic imaging, the cMUT comprising:

a multi-element electrode comprising a first electrode element, a second electrode element, and a third electrode element, the first electrode element being proximate a first side region of the cMUT, the second electrode element being proximate a second side region of the cMUT, and the third electrode element being proximate a middle region of the cMUT;

the first electrode element and the second electrode element forming a side electrode element pair and being electrically coupled to one another to cooperatively shape a membrane of the cMUT during transmission or reception of an ultrasonic signal; and the side electrode element pair being transmit elements, the third electrode element being a receive element, and the first and second electrode elements of the electrode element pair each being so located at side regions of the cMUT to make use of leveraged bending.

23. The cMUT of claim 22, wherein at least one of the first electrode element, the second electrode element, and the third electrode element is a hot electrode of the cMUT.

24. The cMUT of claim 22, wherein at least one of the first electrode element, the second electrode element, and the third electrode element are disposed proximate at least one of a substrate or the membrane.

25. The cMUT of claim 22 further comprising a membrane shaping means, the membrane shaping means including at least one of the first electrode element, the second electrode element, and the third electrode element, the membrane shaping means operatively adapted to shape the membrane in a reception state to receive ultrasonic waves and a transmission state to transmit ultrasonic waves.

26. The cMUT of claim 22, the cMUT further comprising a bottom electrode, wherein the membrane and the bottom electrode are separated by a gap distance in an electrically neutral state, and wherein the side electrode element pair is adapted to flex the membrane by more than one third of the gap distance during transmission of an ultrasonic wave.

27. The cMUT of claim 22, wherein the first electrode element, the second electrode element, and the third electrode element each have a cross sectional width less than the cross sectional width of the membrane.

28. The cMUT of claim 22, wherein the first electrode element, the second electrode element, and the third electrode element are disposed at least partially within the membrane in at least one of a substantially co-planar arrangement or non-planar arrangement with each other.

* * * * *